United States Patent
Widder et al.

(10) Patent No.: US 10,448,661 B2
(45) Date of Patent: Oct. 22, 2019

(54) DRY FOOD COMPOSITION

(75) Inventors: Sabine Widder, Holzminden (DE);
Gerhard Krammer, Holzminden (DE);
Kathrin Langer, Dassel (DE);
Cornelia Hommer, Holzminden (DE)

(73) Assignee: Symrise AG, Holzminden (DE)

( * ) Notice: Subject to any disclaimer, the term of this patent is extended or adjusted under 35 U.S.C. 154(b) by 874 days.

(21) Appl. No.: 14/412,538

(22) PCT Filed: Jul. 6, 2012

(86) PCT No.: PCT/EP2012/063266
§ 371 (c)(1),
(2), (4) Date: Jul. 8, 2015

(87) PCT Pub. No.: WO2014/005649
PCT Pub. Date: Jan. 9, 2014

(65) Prior Publication Data
US 2015/0342238 A1    Dec. 3, 2015

(51) Int. Cl.
| | | |
|---|---|---|
| *A23L 1/30* | (2006.01) | |
| *A23L 33/115* | (2016.01) | |
| *A23L 2/39* | (2006.01) | |
| *A23L 27/00* | (2016.01) | |
| *A23L 27/30* | (2016.01) | |
| *A23L 5/40* | (2016.01) | |
| *A23L 33/00* | (2016.01) | |
| *A23L 33/10* | (2016.01) | |
| *A23L 33/135* | (2016.01) | |
| *A23L 33/15* | (2016.01) | |
| *A23L 33/155* | (2016.01) | |
| *A23L 33/16* | (2016.01) | |
| *A23L 33/17* | (2016.01) | |
| *A23L 33/21* | (2016.01) | |
| *A61K 35/747* | (2015.01) | |
| *A61K 35/745* | (2015.01) | |

(52) U.S. Cl.
CPC .............. *A23L 33/115* (2016.08); *A23L 2/39* (2013.01); *A23L 5/40* (2016.08); *A23L 27/00* (2016.08); *A23L 27/30* (2016.08); *A23L 33/10* (2016.08); *A23L 33/135* (2016.08); *A23L 33/15* (2016.08); *A23L 33/155* (2016.08); *A23L 33/16* (2016.08); *A23L 33/17* (2016.08); *A23L 33/21* (2016.08); *A23L 33/40* (2016.08); *A23V 2002/00* (2013.01); *A61K 35/745* (2013.01); *A61K 35/747* (2013.01)

(58) Field of Classification Search
CPC ........ A23L 1/30; A61K 35/745; A61K 35/747
USPC ............................................. 426/71; 424/439
See application file for complete search history.

(56) References Cited

U.S. PATENT DOCUMENTS

| | | | |
|---|---|---|---|
| 5,490,999 A | | 2/1996 | Villagran |
| 5,688,547 A | * | 11/1997 | Ritchey ................ A23C 9/1546 426/573 |
| 6,489,310 B1 | * | 12/2002 | Brassart .................. A23L 33/22 424/757 |
| 2004/0265360 A1 | * | 12/2004 | Venturi ................... A23L 33/40 424/439 |
| 2005/0271744 A1 | * | 12/2005 | Van Der Heyden ...... A23L 2/52 424/646 |
| 2006/0024412 A1 | * | 2/2006 | Cha .......................... A21D 2/02 426/326 |
| 2006/0286270 A1 | * | 12/2006 | Jordan .................... A23P 30/20 426/620 |
| 2007/0231371 A1 | * | 10/2007 | Pan ....................... A61K 31/095 424/442 |
| 2008/0193598 A1 | * | 8/2008 | Solomon .............. A23C 9/1206 426/61 |

FOREIGN PATENT DOCUMENTS

WO       80/02226 A1    10/1980

OTHER PUBLICATIONS

Ziegler et al, "The role of particle size distribution of suspended solids in defining the sensory properties of milk chocolate," XP002693146, Database accession No. FS-2001-12-Ka0325 & International Journal of Food Properties, vol. 4, No. 2, 2011, p. 353.
Imai et al, "Effect of Physical Properties of Food Particles on the Degree of Graininess Perceived in the Mouth," Journal of Texture Studies, vol. 30, No. 1, May 1, 1999, pp. 59-88.

* cited by examiner

*Primary Examiner* — Bhaskar Mukhopadhyay
(74) *Attorney, Agent, or Firm* — Dilworth & Barrese, LLP

(57) ABSTRACT

Suggested is a dry food composition for mixing with a drinkable liquid, said composition comprising (a) carbohydrates, (b) proteins, (c) fats, and optionally (d) probiotic micro-organisms and/or prebiotics, and (e) vitamins, minerals, texturizers, fibers, sweeteners, flavorings and/or colorants, whereby said composition shows a particle size distribution wherein (i) about 90% b.w. of the particles show an average diameter of less than about 400 µm, (ii) about 50% b.w. of the particles show an average diameter of less than about 80 µm, and (iii) about 10% b.w. of the particles show an average diameter of less than about 10 µm.

20 Claims, 1 Drawing Sheet

Figure 1:
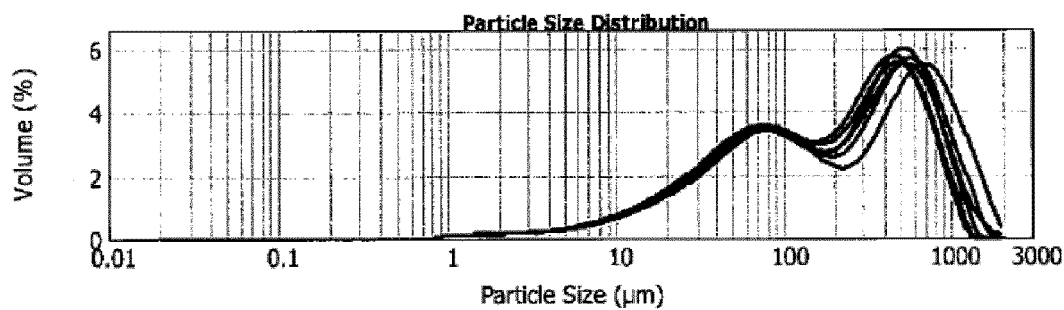

Particle size distribution of the composition of Example 1 before milling

Particle size distribution of the composition of Example 1 after milling

DRY FOOD COMPOSITION

FIELD OF INVENTION

The present invention belongs to the area of nutrition and refers to a new natural balance shake that has improved taste and texture.

STATE OF THE ART

Even though the importance of balanced diets has been recognized by dietitians and scientists as well as by the general public for a long time, the maintenance of a healthy diet is not only a persisting but also a growing problem in modern society. With today's accelerated pace of living, it has become increasingly difficult for ordinary people to find the time to prepare meals ensuring a daily intake of nourishment essential to the human body.

The lack of time makes many people choose fast food alternatives, which often are fattening or have an inadequate nutritive value, or even skip entire important meals such as breakfast.

A further problem occurs in the composing of the food components. Even though there is a high awareness in the general public of which essential nutritive components should be included in an ordinary meal, very often in daily life it becomes difficult to estimate the amount of nutrients in the different ingredients constituting the meal. As the different food components are known to interact with each other, the total nutritive effect of the meal may be furthermore difficult to estimate. Especially the effect of the absorbed food on the blood glucose level has shown to be of great importance for the well-being of humans. When food is eaten, digested and absorbed into the blood stream, a corresponding rise can be detected in the blood glucose level. Poorly balanced diets often include carbohydrates which, when converted to glucose, induce a rapid response of insulin. The so-called insulin spikes lead to a rapid storage of sugar, and subsequently also fat, into the cells, thus giving rise to an unnecessary amount of energy being stored in the body. Accordingly, shortly after the first meal, the blood glucose level in the blood is considerably reduced by the correspondingly rapid action of insulin and the body signals for more glucose with feelings of hunger, tiredness, lack of concentration etc.

Because of the direct need for an increase of the blood glucose level, a craving for foodstuffs with high sugar content is induced, again starting a new cycle of drastic fluctuations in the blood glucose level, when provided with further glucose. These swift fluctuations in the blood glucose level leave the consumer with temperamental ups and downs, and invite the consumer to a habit of constant eating which also becomes a problem in controlling the weight, and furthermore also will add fat to the heart and the blood system.

It is also important to note that in order to satisfy feelings of hunger, not all foodstuffs have proven to have a long term satiating effect. As the hungry consumer strives to balance the blood glucose level, a further problem occurs in the difficulty of choosing foodstuffs able to provide satiety for a prolonged period of time.

From the state of the art food compositions meeting these needs are already known.

For example, international patent application WO 1980 002226 A1 (Elaine Powers) refers to a dry nutritious food composition adapted for mixing with water to form an aqueous dispersion having a pleasing palatable taste with improved filling characteristics which is useful as a total meal replacement and which contains protein selected from the group consisting of casein, calcium caseinate, sodium caseinate and non-fat milk solids, lipids, carbohydrates and non-degradable vegetable fibre in the form of cellulose gum and cellulose gel and containing added vitamins, trace minerals and flavouring agents.

A composition and method for providing nutrition is subject to EP 0691079 A1 (Clinic Nutrition). The product is low in carbohydrates, and high in fats. The fat comprises, in part, medium chain triglycerides (MCTs). Preferably, the composition includes a high percent of monounsaturated fats, high amylose starch, and soluble dietary fibre.

An enteral composition which contains a protein source, a lipid source, a carbohydrate source, and a fibre blend is known from EP 1010374 A1 (Nestle). The fibre blend contains inulin and fructo-oligosaccharides and has 45 to 55% b.w. of the blend of soluble fibres and 45 to 55% b.w. of the blend of insoluble fibres. The product may also contain pea inner fibres and pea outer envelope fibres.

U.S. Pat. No. 5,104,676 (Mahmoud) suggests a weight control product that is preferably in the form of agglomerated particles and is reconstitutable in water. The product contains low lactose milk and a dietary fibre system which is a particular blend of soluble, insoluble, fermentable and non-fermentable fibres. The components of the dietary fibre system are oat hull fibre, gum arabic and sodium carboxymethylcellulose.

U.S. Pat. No. 5,998,363 (Bell) refers to an improved enteral formulation that is low in fat and contains protein hydrolysates. The osmolality of the formulation is controlled to be below 500 mOs/kg $H_2O$, and preferably about 300 mOs/kg $H_2O$. In a preferred embodiment, the formulation contains corn starch to control blood glucose levels. This formulation is particularly useful for treatment of critically ill patients and in minimizing a risk of pulmonary aspiration and/or gastrointestinal dysfunction in such patients.

International patent application WO 2002 011562 A1 (Functional Foods Inc.) discloses nutritional supplements and methods to aid with the management of weight loss for overweight and obese pediatric patients are described. The nutritional supplement comprises a low-glycaemic-index carbohydrate source, a source of protein and a source of fat. The product may be in the form of an extruded bar, powder or beverage.

International patent application WO 2004 017764 A1 (Indevex) teaches a composition comprising fat, carbohydrates, proteins, vitamins and minerals comprising said components in amounts that an intake of said food composition provides the consumer with a stable blood glucose level.

A serious disadvantage of the products known from the state of the art and in particular with respect to the dry food compositions of WO 2004 017764 A1 is their insufficient performance with respect to taste and texture. The products are recognised as being gritty, providing a sandy feeling on the tongue and in the throat, and a bitter and astringent taste. In addition the bioavailability of the valuable components, especially of the proteins, is often poor. At the end of the day, consumers are not willing to buy these products, although their advantages for the health status of a human are beyond doubt.

Therefore, the problem underlying the present invention has been to develop a food composition that is easy to dispense in a drinkable liquid to provide a natural balance shake, showing better performance with respect to taste, texture and bioavailability of the value components compared to the products one can find in the market, in order to achieve a better consumer acceptance.

DESCRIPTION OF THE INVENTION

Suggested is a dry food composition for mixing with a drinkable liquid, said composition comprising
(a) carbohydrates,
(b) proteins,
(c) fats, and optionally
(d) probiotic micro-organisms and/or prebiotics, and
(e) vitamins, minerals, texturisers, fibres, sweeteners, flavourings and/or colorants, whereby said composition shows a particle size distribution wherein
  (i) about 90% b.w. of the particles show an average diameter of less than about 400 μm, preferably less than about 100 μm,
  (ii) about 50% b.w. of the particles show an average diameter of less than about 80 μm, preferably less than about 40 μm and
  (iii) about 10% b.w. of the particles show an average diameter of less than about 10 μm, preferably less than about 0.1 μm.

Preferably the food composition of the invention when mixed with a drinkable liquid shows glycaemic index (GI) of less than 30, more preferably less than 20, and most preferably less than 10. The glycaemic index is a measure of the degree to which the concentration of glucose in the blood rises after consumption of certain foodstuffs. A low GI here refers to foodstuffs with a value between 0 and 55. The GI may be calculated using two different references, that is to say either the reference white bread or the reference glucose. In the measurements made on the food composition product according to the invention, the reference glucose was utilised. In order to estimate the overall glycaemic effect of a meal, the concept of "glycaemic load" (GL) (GI×dietary carbohydrate content) has been introduced. As the GI compares corresponding amounts of carbohydrates, providing a measure of carbohydrate quantity, but not quality, the GL-value provides the glycaemic effect of realistic portion sizes of different foods. The GL-value is similar to the GI-value, a measure of the rise of the blood glucose and the subsequent secretion of insulin in the blood stream, but including the aspect of the amount of carbohydrates available in a portion of food (see Foster-Powell K., et al. *J. Clin. Nutr.* 76:5-56, 2002).

In order to achieve a low GI it is advantageous to adjust the ratio by weight between carbohydrates, proteins and fat to a value of about 0.5 to 2.0:1:0.1 to 0.4., preferably 0.6 to 1.5:1:0.1 to 0.3.

Surprisingly it has been observed that grinding the complete composition in order to achieve a particle size distribution as set out above improves the over-all texture. The compositions are pleasantly smooth and viscous, creamy, provide more body, but are less astringent and bitter, so that the consumer acceptance is significantly higher. It was also found that bioavailability of value components, in particular of proteins is significantly improved. Adding one or more of the components forming the groups (d) and (e), in particular adding prebiotics, sweeteners and flavours, leads to another improvement of taste and texture. If not indicated otherwise the following amounts are calculated on the dry food composition.

The grinding of the compositions can be conducted by using any conventional mill. Particularly preferred, however, are ball mills and preferably planetary ball mills. A ball mill represents a cylindrical device used in grinding (or mixing) materials like ores, chemicals, ceramic raw materials and paints. Ball mills rotate around a horizontal axis, partially filled with the material to be ground plus the grinding medium. Different materials are used as media, including ceramic balls, flint pebbles and stainless steel balls. An internal cascading effect reduces the material to a fine powder. Industrial ball mills can be operated continuously, being fed at one and being discharged at the other end. Large to medium-sized ball mills are mechanically rotated on their axis, but small ones normally consist of a cylindrical capped container that sits on two drive shafts (pulleys and belts are used to transmit rotary motion). A rock tumbler functions on the same principle. High-quality ball mills can grind mixture particles to as small as 5 nm, enormously increasing surface area. The grinding works on the principle of critical speed. The critical speed can be understood as that speed after which the steel balls, which are responsible for the grinding of particles, start rotating along the direction of the cylindrical device; thus causing no further grinding.

A. Carbohydrates

According to one preferred embodiment of the invention, the carbohydrates (component a) are derived from leguminous plants, preferably yellow peas, and rosaceous plants, preferably apples and rose hips, wherein said leguminous plants and rosaceous plants contribute in giving the food composition product its advantageously low GL-value. However, carbohydrates may, of course within the scope of the invention, be chosen from other plants having a low glycaemic index. Apples and rose hips may furthermore be substituted with pears, peaches, plums, or the like, all of which being rosaceous plants with a low glycaemic index. In a further preferred embodiment of the invention, at least about 12% b.w. of the overall content of the food composition product is derived from yellow peas, at least about 10% b.w. from apples and at least about 5% b.w. from rose hips. The content of the mentioned ingredients preferably does not exceed about 30% b.w. for yellow peas, about 25% b.w. for apples, and about 15% b.w. for rose hips so as to maintain the important balance between carbohydrates, proteins and fat. A study performed by the present inventors on a food composition product including vitaceous plants has shown that such an inclusion significantly increases the GL-value for the overall food composition product.

According to a further embodiment of the invention, the carbohydrates, when decomposed provide the human body system with simple sugars from the group consisting of glucose, saccharose, fructose, maltose and lactose. The different sugars are advantageously present in an amount of
(a1) about 2.1 to about 3% b.w., and preferably less than 2.7% b.w. glucose;
(a2) about 1.0 to about 2.2% b.w., and preferably less than 2.0% b.w. saccharose;
(a3) about 4.0 to about 8.0% b.w., and preferably less than 6.0% b.w. fructose;
(a4) less than about 0.05% b.w., and preferably less than about 0.04% b.w., maltose; and
(a5) about 7.5 to about 13.7% b.w., and preferably less than 10% b.w. lactose.

However, it is also possible to alter the contents of the different types of sugar within the scope of the invention. In one embodiment according to the invention the food composition product is low lactose or completely free from lactose in order to meet the demands for such products. A low lactose product is directed to people who cannot tolerate milk, and thus lactose, in small amounts. It is important to note that the ready to drink product—when one serving of the food composition product consisting of about 18 g powder is mixed with at least 20 cl water—gives less than 1% b.w. lactose content per serving, which is to be recognized as low lactose content.

B. Proteins

The food composition of the present invention also encompasses proteins (component b). More particularly the compositions comprise proteins in an amount of about 30 to about 45 g, more preferably about 35 to about 40 g, and most preferably about 37 to about 39 g per 100 g dry food composition powder), thus containing all 20 amino acids including the 8 recognized essential amino acids in physiological doses. The amino acids are suitably derived from sources such as whey, yellow pea, soy, potatoes, lupine, egg albumen, and whole eggs. The food composition product according to the invention is designed to ensure that a daily allowance of proteins, and essential amino acids, is met. The content of protein is further designed so that the composition of the food composition product provides a positive nitrogen balance which promotes water excretion, visceral fat utilisation and lean body mass preservation.

C. Fats

In a preferred embodiment according to the invention the fat (component c) of the food composition product comprises the essential fatty acids with an omega-3 to omega-6 fatty acid ratio of 1:0.5 to 1:3.0, more preferably 1:0.8 to 1:2.0, and most preferably 1:1.0 to 1:1.3. A correct balance is significant in order to maintain normal cellular and other functions. As a typical western diet consists of far more omega-6 fatty acids than omega-3 fatty acids, many meals are lacking the essential amount of the desired fatty acids and have moreover an inadequate balance of said fatty acids. The fat of the product is further composed to meet the needs for saturated, and mono-, di-, tri- and polyunsaturated fatty acids.

In a preferred embodiment of the invention the fat comprises (c1) about 25 to about 40% b.w., preferably about 28 to about 35% b.w., and more preferably about 29 to about 33% b.w., saturated fatty acids, (c2) about 30 to about 45% b.w., preferably about 32 to about 39% b.w., and more preferably about 33 to about 37% b.w., monounsaturated fatty acids, and (c3) about 15 to about 35% b.w., preferably about 25 to about 35% b.w., and more preferably about 29 to about 33% b.w., di- and tri-unsaturated fatty acids.

Polyunsaturated fatty acids are preferably present in an amount of 3.0 to 3.6% b.w. The balance between the three main groups of fatty acids is thus optimised. Respective products that are found in the market are known for example under the trademark Omacor® (Pronova Biosicience A.S.)

In the alternative the fats may also contain conjugated linoleic acid (CLA) as a main constituent of its fatty acid part. Such glycerides are sold for example under the trademark Tonalin® (BASF Personal Care & Nutrition GmbH).

The content of fat in a properly balanced meal is essential; fats contain important fat soluble vitamins and essential fatty acids which cannot be produced by the human body. The fatty acids are preferably chosen from the group consisting of myristic acid, palmitic acid, palmitoleic acid, heptadecanoic acid, stearic acid, oleic acid, linoleic acid, alfa-linolenic acid, arachidic acid, eicosadienoic acid, behenic acid, docosahexaenoic acid (DHA) and eicosapentaenoic acid (EPA). However, the invention is not restricted to the fatty acids mentioned herein. Other fatty acids which are within the scope of the invention may also be chosen. In addition, the levels of docosahexaenoic acid (DHA) and eicosapentaenoic acid (EPA) are optimised and constitute between about 1.9 to about 2.3% b.w., preferably about 2.1% b.w. of the total fat. Cholesterol is also present in amounts which meet the body's needs. Preferably, the fat of the food composition product is mainly derived from whole eggs.

To achieve the preferred balance between saturated, monounsaturated and polyunsaturated fat for example the whole egg content in the food composition product is supplied from especially fed chicken in order to give the whole egg product a balance between omega-3 and omega-6 fatty acids in a rating of 1:0.7 to 1.5.

D1. Probiotic Micro-Organisms

Probiotic organisms, also called "probiotics" forming component (d1) represent live microorganisms which are considered to be beneficial to the host organism. According to the currently adopted definition by FAO/WHO, probiotics are: "Live microorganisms which when administered in adequate amounts confer a health benefit on the host". Lactic acid bacteria (LAB) and bifidobacteria are the most common types of microbes used as probiotics; but certain yeasts and bacilli may also be used. Probiotics are commonly consumed as part of fermented foods with specially added active live cultures; such as in yogurt, soy yogurt, or as dietary supplements. Live probiotic cultures are available in fermented dairy products and probiotic fortified foods. However, tablets, capsules, powders and sachets containing the bacteria in freeze dried form are also available. Table A provides an overview of common probiotics and their respective health claims that can be used as component (d1) of the present invention:

TABLE A

| | Probiotics | | |
|---|---|---|---|
| Strain | Brand name | Producer | Health claims |
| *Bacillus coagulans* GBI-30, 6086 | GanedenBC | Ganeden Biotech | May improve abdominal pain and bloating in IBS patients. May increase immune response to a viral challenge. |
| *Bifidobacterium animalis* subsp. *lactis* BB-12 | Probio-Tec *Bifidobacterium* BB-12 | Chr. Hansen | Human studies have shown that BB-12 alone or in combination may have an effect on the gastrointestinal system. |
| *Bifidobacterium infantis* 35624 | Align | Procter & Gamble | In one preliminary study, showed possible improvement for abdominal pain/discomfort and bowel movement difficulty. |

TABLE A-continued

Probiotics

| Strain | Brand name | Producer | Health claims |
|---|---|---|---|
| Lactobacillus acidophilus NCFM | | Danisco | Shown in one study to reduce the side effects of antibiotic therapy. |
| Lactobacillus paracasei St11 (or NCC2461) | | | |
| Lactobacillus johnsonii La1 (=Lactobacillus LC1, Lactobacillus johnsonii NCC533) | | Nestlé | May reduce incidence of H pylori-caused gastritis and may reduce inflammation |
| Lactobacillus plantarum 299v | GoodBelly/Pro-Viva/ProbiMage | Probi | May improve symptoms of IBS; however, more research is required. |
| Lactobacillus reuteri American Type Culture Collection | ATTC 55730 (Lactobacillus reuteri SD2112) | | BioGaia | Preliminary evidence for diarrhea mitigation in children, H. pylori infection, possible effect on gingivitis, fever in children and number of sick days in adults. |
| Lactobacillus reuteri Protectis (DSM 17938, daughter strain of ATCC 55730) | Lactobacillus reuteri Protectis (DSM 17938, daughter strain of ATCC 55730) | Lactobacillus reuteri Protectis (DSM 17938, daughter strain of ATCC 55730) | Lactobacillus reuteri Protectis (DSM 17938, daughter strain of ATCC 55730) |
| Saccharomyces boulardii | DiarSafe and others | Wren Laboratories | Limited evidence for treatment of acute diarrhea. |
| Lactobacillus rhamnosus GR-1 & Lactobacillus reuteri RC-14 | Bion Flore In-time/Jarrow Fem-Dophilus | Chr. Hansen | In one study, oral ingestion resulted in vaginal colonisation and reduced vaginitis. |
| Lactobacillus acidophilus NCFM & Bifidobacterium bifidum BB-12 | Florajen3 | American Lifeline, Inc | Preliminary evidence for reduced C. difficile-associated disease (CDAD). |
| Lactobacillus acidophilus CL1285 & Lactobacillus casei LBC80R | Bio-K+ CL1285 | Bio-K+ International | May affect digestive health. In vitro inhibition of Listeria monocytogenes and L. innocua, Escherichia coli, Staphylococcus aureus, Enterococcus faecalis and Enterococcus faecium. Reduction of symptoms of lactose intolerance and immune stimulation.[86] |
| Lactobacillus plantarum HEAL 9 & Lactobacillus paracasei 8700:2 | Bravo Friscus/ProbiFrisk | Probi | Is under study for common cold infections. |

Some additional forms of lactic acid bacteria, representing also suitable probiotics include:
  Lactobacillus bulgaricus;
  Streptococcus thermophilus;
  "Lactobacillus bifidus"—became new genus Bifidobacterium.

Some fermented products containing similar lactic acid bacteria include:
  Pickled vegetables
  Fermented bean paste such as tempeh, miso and doenjang;
  Kefir;
  Buttermilk or Karnemelk;
  Kimchi;
  Pao cai;
  Soy sauce;
  Zha cai.

Said probiotic microorganisms may be present in the food composition in amounts of about 1 to about 10% b.w., and preferably about 2 to about 5% b.w.

D2. Prebiotics

In another embodiment of the present invention the food compositions may include prebiotics. Prebiotics are defined as non-digestible food ingredients that may beneficially affect the host be selectively stimulating the growth and/or the activity of a limited number of bacteria in the colon. Adding prebiotics to the compositions leads to another improvement of the stability of the anthocyanins against degradation within the intestine. The following describes in particular various oligosaccharides which can be taken into account as suitable prebiotics (component d2):

Fructooligosaccharides. Fructooligosaccharides or FOS typically refer to short-chain oligosaccharides comprised of D-fructose and D-glucose, containing from three to five monosaccharide units. FOS, also called neosugar and short-chain FOS, are produced on a commercial scale from sucrose using a fungal fructosyltransferase enzyme. FOS are resistant to digestion in the upper gastrointestinal tract. They act to stimulate the growth of Bifidobacterium species in the large intestine. FOS are marketed in the United States in combination with probiotic bacteria and in some functional food products.

Inulins. Inulins refer to a group of naturally-occurring fructose-containing oligosaccharides. Inulins belong to a class of carbohydrates known as fructans. They are derived from the roots of chicory (*Cichorium intybus*) and Jerusalem artichokes. Inulins are mainly comprised of fructose units and typically have a terminal glucose. The bond between fructose units in inulins is a beta-(2-1) glycosidic linkage. The average degree of polymerisation of inulins marketed as nutritional supplements is 10 to 12. Inulins stimulate the growth of *Bifidobacterium* species in the large intestine.

Isomaltooligosaccharides. Isomaltooligosaccharides comprise a mixture of alpha-D-linked glucose oligomers, including isomaltose, panose, isomaltotetraose, isomaltopentaose, nigerose, kojibiose, isopanose and higher branched oligosaccharides. Isomaltooligosaccharides are produced by various enzymatic processes. They act to stimulate the growth of *Bifidobacterium* species and *Lactobacillus* species in the large intestine. Isomalto oligosaccharides are marketed in Japan as dietary supplements and in functional foods. They are being developed in the United States for similar uses.

Lactilol. Lactilol is a disaccharide analogue of lactulose. Its pharmaceutical use is in the treatment of constipation and hepatic encephalopathy. Lactilol is also used in Japan as a prebiotic. It is resistant to digestion in the upper gastrointestinal tract and it is fermented by a limited number of colonic bacteria, resulting in an increase in the biomass of bifidobacteria and lactobacilli in the colon. Lactilol is known chemically as 4-0-(beta-D-galactopyranosyl)-D-glucitol. Lactilol is not approved for the treatment of hepatic encephalopathy or constipation in the U.S., and its use as a prebiotic is considered experimental. Lactilol is used in Europe as a food sweetener.

Lactosucrose. Lactosucrose is a trisaccharide comprised of D-galactose, D-glucose and D-fructose. Lactosucrose is produced enzymatically by the enzymatic transfer of the galactosyl residue in lactose to sucrose. Lactosucrose is resistant to digestion in the stomach and small intestine. It is selectively utilized by intestinal *Bifidobacterium* species resulting in significant induction of growth of these bacteria in the colon. Therefore, under physiological conditions, lactosucrose acts on the intestinal microflora as a growth factor for *Bifidobacterium* species. Lactosucrose is also known as 4G-beta-D-galactosylsucrose. It is widely used in Japan as a dietary supplement and in functional foods, including yoghurt. Lactosucrose is being developed in the United States for similar uses.

Lactulose. Lactulose is a semi-synthetic disaccharide comprised of the sugars D-lactose and D-fructose. The sugars are joined by a beta-glycosidic linkage, making it resistant to hydrolysis by human digestive enzymes. Lactulose is, however, fermented by a limited number of colonic bacteria. This can lead to changes in the colonic ecosystem in favour of bacteria, such as lactobacilli and bifidobacteria, which may confer some health benefits. Lactulose is a prescription drug in the United States for the treatment of constipation and hepatic encephalopathy. It is marketed in Japan for use as a dietary supplement and in functional foods. Its use in the United States as a prebiotic substance is still experimental.

Pyrodextrins. Pyrodextrins comprise a mixture of glucose-containing oligosaccharides that is derived from the hydrolysis of starch. Pyrodextrins have been found to promote the proliferation of *Bifidobacterium* species in the large intestine. They are resistant to digestion in the upper gastrointestinal tract. Pyrodextrins are being developed for the nutritional supplement market place.

Soy oligosaccharides. Soy oligosaccharides refer to oligosaccharides found in soybeans and also in other beans and peas. The two principal soy oligosaccharides are the trisaccharide raffinose and the tetrasaccharide stachyose. Raffinose comprises one molecule each of D-galactose, D-glucose and D-fructose. Stachyose consists of two molecules of D-galactose, one molecule of D-glucose and one molecule of D-fructose. Soy oligosaccharides act to stimulate the growth of *Bifidobacterium* species in the large intestine. They are marketed in Japan as dietary supplements and in functional foods. They are being developed in the United States for similar uses.

Transgalactooligosaccharides. Transgalactooligosaccharides (TOS) are a mixture of oligosaccharides consisting of D-glucose and D-galactose. TOS are produced from D-lactose via the action of the enzyme beta-galactosidase obtained from *Aspergillus oryzae*. TOS are resistant to digestion in the upper gastrointestinal tract and stimulate the growth of bifidobacteria in the large intestine. TOS are marketed in Japan and Europe as dietary supplements and are used in functional foods. They are being developed for similar use in the United States.

Xylooligosaccharides. Xylooligosaccharides are comprised of oligosaccharides containing beta (1? 4) linked xylose residues. The degree of polymerisation of xylooligosaccharides is from two to four. Xylo oligosaccharides are obtained by enzymatic hydrolysis of the polysaccharide xylan. They are marketed in Japan as prebiotics and are being developed for similar use in the United States.

Biopolymers. Suitable biopolymers like e.g. beta-glucans include those originating from plants including cereals such as oats and barley, fungi, yeast, and bacteria. In addition, microbial cell wall preparations and whole cells rich in beta glucans are also suitable sources for beta glucan preparations useful for the present invention. Monomer residues in glucans can have 1-3 and 1-4, or 1-3 and 1-6 linkages (that is the monomer units are joined through 1,3, 1,4 or 1,6 bonds) and the percent of each type can vary. Preferably, beta glucans derived from yeast, particularly from *Saccharomyces*, preferably *Saccharomyces cerevisiae*, are used for the present invention. It will be appreciated, however, that other beta glucans would also be suitable. Further examples for suitable biopolymers are chitin and its derivatives, preferably oligoglucosamin and chitosan which represent a typical hydrocolloid.

Said prebiotics may be present in the food composition in amounts of about 2 to about 25% b.w., preferably about 12 to about 20% b.w., and more preferably about 15 to 18% b.w.

E1. Vitamins

In another embodiment of the present invention the compositions may include vitamins (component e1). Vitamins have diverse biochemical functions. Some have hormone-like functions as regulators of mineral metabolism (e.g., vitamin D), or regulators of cell and tissue growth and differentiation (e.g., some forms of vitamin A). Others function as antioxidants (e.g., vitamin E and sometimes vitamin C). The largest number of vitamins (e.g., B complex vitamins) act as precursors for enzyme cofactors, that help enzymes in their work as catalysts in metabolism. In this role, vitamins may be tightly bound to enzymes as part of prosthetic groups: For example, biotin is part of enzymes involved in making fatty acids. Vitamins may also be less tightly bound to enzyme catalysts as coenzymes, detachable molecules that function to carry chemical groups or electrons between molecules. For example, folic acid carries various forms of carbon group—methyl, formyl, and methylene—in the cell. Although these roles in assisting enzyme-substrate reactions are vitamins' best-known function, the other vitamin functions are equally important. In the course of the present invention suitable vitamins are selected from the group consisting of Vitamin A (retinol, retinal, beta carotene),
Vitamin $B_1$ (thiamine),
Vitamin $B_2$ (riboflavin),
Vitamin $B_3$ (niacin, niacinamide),
Vitamin $B_5$ (panthothenic acid),
Vitamin $B_6$ (pyridoxine, pyridoxamine, paridoxal),
Vitamin $B_7$ (biotin),
Vitamin $B_9$ (folic acid, folinic acid),
Vitamin $B_{12}$ (cyanobalamin, hydoxycobalmin, methylcobalmin),
Vitamin C (ascorbic acid),
Vitamin D (cholecalciferol),
Vitamin E (tocopherols, tocotrienols), and
Vitamin K (phyolloquinone, menaquinone).

The preferred vitamins are ascorbic acid and tocopherols.

Said vitamins may be present in the food composition in amounts of about 0.1 to about 5% b.w., and preferably about 0.5 to about 1% b.w.

E2. Minerals

In another embodiment of the present invention the compositions may include minerals (component e2) that are selected from the group consisting of aluminium, antimony, arsenic, barium, beryllium, boron, bromide, cadmium, cerium, caesium, chloride, chrome, dysprosium, iron, erbium, europium, fluoride, gadolinium, gallium, germanium, gold, hafnium, holmium, indium, iridium, iodide, potassium, calcium, cobalt, copper, lanthanum, lithium, lutetium, magnesium, manganese, molybdenum, sodium, neodymium, nickel, niobium, osmium, palladium, phosphorus, platinum, praseodymium, rhenium, rhodium, rubidium, ruthenium, samarium, scandium, sulphur, selenium, silica, silver, strontium, tantalum, tellurium, terbium, thallium, thorium, thulium, titan, vanadium, ytterbium, yttrium, bismuth, wolfram, zinc, tin, zirconium, and their mixtures. The preferred mineral is zinc. The minerals can be added to the dietary supplement compositions in the form of their pharmaceutically acceptable salts.

Said minerals may be present in the food composition in amounts of about 100 to about 2000 ppm, and preferably about 500 to about 1000 ppm.

E3, E4. Texturisers and Fibres

Suitable texturisers (component e3) encompass chemically modified starch products, such as for example carboxymethylcelluloses.

The composition may also contain physiological doses of dietary fibres (component e4). The GI of a meal is affected by the content of fibres, as a high degree of fibres helps to lower the glycaemic index. Fibres are not digested, but are however necessary in order for the bowels to function correctly. The high content of fibres in the food composition product according to the invention is advantageous in improving motility (bowel movements) and thus enhancing the consumer's ability to process food efficiently. In addition, the fibres support the elimination of toxins in the cells and furthermore are recognized to reduce the cholesterol content in the blood system. Typically the amount of texturisers and/or fibres lies in the range of about 0.1% to about 12% b.w.

E5. Sweeteners

Suitable sweet-tasting substances, including natural sources of these substances (component e5), such as for example sweet-tasting carbohydrates or sugars (e.g. sucrose (synonymous with saccharose), trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrin) or vegetable preparations containing predominantly these carbohydrates (e.g. from sugar beet (*Beta vulgaris* ssp., sugar fractions, sugar syrup, molasses), from sugar cane (*Saccharum officinarum* ssp., e.g. molasses, sugar syrups), from sugar maple (*Acer* ssp.), from agave (agave thick juice), synthetic/enzymatic hydrolysates of starch or sucrose (e.g. invert sugar syrup, highly enriched fructose syrups made from corn starch), fruit concentrates (e.g. from apples or pears, apple syrup, pear syrup), sugar alcohols (e.g. erythritol, threitol, arabitol, ribitol, xylitol, sorbitol, mannitol, dulcitol, lactitol), proteins (e.g. miraculin, monellin, thaumatin, curculin, brazzein), sweeteners (magap, sodiumcyclamate, acesulfame K, neohesperidin dihydrochalcone, saccharin sodium salt, Aspartame®, superaspartame, neotame, alitame, sucralose, stevioside, rebaudioside, lugduname, carrelame, sucrononate, sucrooctate, monatin, phyllodulcin), certain sweet-tasting amino acids (glycine, D-leucine, D-threonine, D-asparagine, D-phenylalanine, D-tryptophan, L-proline), other sweet-tasting low-molecular substances (e.g. hernandulcin, dihydrochalcone glycosides, glycyrrhizin, glycyrrhetinic acid ammonium salt or other glycyrrhetinic acid derivatives), liquorice extracts (*Glycyrrhizza glabra* ssp.), *Lippia dulcis* extracts, *Momordica* ssp. extracts or individual substances (in particular *Momordica grosvenori* [Luo Han Guo] and the mogrosides obtained therefrom), *Hydrangea dulcis* or *Stevia* ssp. (e.g. *Stevia rebaudiana*) extracts or individual substances.

E6. Flavourings

Flavourings are a mixture of volatile and non volatile compounds which are used to improve or modify the odour and or taste of foods for the benefit of the consumer. Flavourings are typically used to compensate the loss of flavour during processing and storage of foods such as pasteurization to compensate for natural seasonal or geographical variations in crops to compensate the unpleasant odour and taste of food ingredients to compensate the reduction of sugar, fat and salt in food to provide novel and innovative concepts Typically the amount flavourings lies in the range of about 0.001 to about 5% b.w., and preferably about 0.01 to about 2% b.w.

Food Composition

The mutual relation between carbohydrates, proteins and fat in the food composition product has surprisingly been proven to be of significant value in maintaining the overall body system in balance, which is, avoiding deficiencies and excesses of nutrients in the systems of the body. When the body is in balance, intake of nutrients and energy is sufficient to maintain tissue needs and the amounts of nutrients and energy entering and exiting the body are equal. The above mentioned relation further provides the consumer with an amount of each component corresponding to an adequate meal when being provided with a portion of the food composition product according to the invention.

In a preferred embodiment the food compositions of the present invention comprise carbohydrates, proteins and fats in the following ratios:
(a) about 10 to about 20% b.w., preferably about 12 to about 18% b.w, and more preferably about 12 to about 15% b.w. whole eggs;
(b) about 3 to about 15% b.w., preferably about 6 to about 12% b.w, and more preferably about 8 to about 10% b.w. egg albumin;
(c) about 10 to about 25% b.w., preferably about 12 to about 20% b.w, and more preferably about 14 to about 16% b.w. whey protein concentrate;
(d) about 10 to about 35% b.w., preferably about 10 to about 25% b.w, and more preferably about 15 to about 22% b.w. yellow pea;
(e) about 10 to about 25% b.w., preferably about 12 to about 22% b.w, and more preferably about 15 to about 20% b.w. apple powder; and
(f) about 5 to about 15% b.w., preferably about 7 to about 10% b.w, and more preferably about 9 to 10% b.w. rose hips powder,
on condition that the amounts add optionally with additional ingredients to 100% b.w.

The food composition product is balanced with ingredients so that it offers a complete meal with less than about 75 kcal per portion serving, more preferably less than about 70 kcal, and most preferably less than about 68 kcal, and correspondingly less than about 425 kcal, more preferably less than about 400 kcal, and most preferably less than about 385 kcal per 100 g powder mix of the dry food composition product. The term serving here refers to a portion of the dry food composition product when dispersed in a drinkable liquid.

Also preferred is an embodiment according to which the composition shows when mixed with a drinkable liquid a pH-value in the range of 5.8 to 6.2. These compositions act like a buffer, thus having a positive effect on people suffering from G.E.R.D (gastroesophageal reflux disease) and Non Ulcer Dyspepsia.

Even more preferred are compositions which are essentially free of gluten, which means that the gluten content is either 0 or within a range of 0.1 to 0.01% b.w.

INDUSTRIAL APPLICATION

Another object of the present invention is directed to a non-therapeutic method for improving the over-all health status of a human body by consumption of a dry food composition comprising
(a) carbohydrates,
(b) proteins,
(c) fats, and optionally
(d) probiotic micro-organisms and/or prebiotics, and
(e) vitamins, minerals, texturisers, fibres, sweeteners, flavourings and/or colorants, whereby said composition shows a particle size distribution wherein
  (i) about 90% b.w. of the particles show an average diameter of less than about 400 μm, preferably less than about 100 μm,
  (ii) about 50% b.w. of the particles show an average diameter of less than about 80 μm, preferably less than about 40 μm and
  (iii) about 10% b.w. of the particles show an average diameter of less than about 10 μm, preferably less than about 0.1 μm.

Because of the demand for a balanced meal which is ready to use, the food composition product is preferably pre-packed in a dry powder form in single portion packs with a net dry weight of preferably about 15 to about 20 g, more preferably about 18 to about 19 g. The dry powder is readily dispersed in a drinkable liquid, preferably water, and may be consumed promptly. Missing out on meals such as breakfast, or eating fast food or snacks, due to a tight schedule may thus be avoided, and a healthy lifestyle can be maintained. In order to replace a breakfast, one or two single portion packs are preferably used, depending on the individuals need. Children are suitably provided with one single portion pack for breakfast, while adults suitably are required to consume one to two single portion packs. In order to obtain a proper intake of nourishment equivalent with a dinner, males should consume up to four single portion packs, while women are required to consume up to three. The consumption of said product should, however, not exceed more than an equaling number of portion packs containing about 7 g of protein each corresponding to a daily intake of 0.75 g protein per kilogram body weight. The dry powder has proven to be advantageously stable to degradation, especially with regard to fatty acids, for at least three months in 25° C. and 40° C., respectively. The prepacking of the food composition product also prevents exposure to air and moisture, and subsequent oxidation, when compared to packages where the consumer is intended to serve out a portion from a larger quantity of dry powder.

Said product may also be mixed with a drinkable liquid, such as milk, juice or the like. When the food composition product is mixed with juice, the content of carbohydrates is increased, providing consumers with greater needs for carbohydrates, such as growing children, to have a meal with higher energy content.

Furthermore, said food composition product may also be produced in the form of a bar, thus providing the consumer with one or more portions of the food composition product in an expediently packaged form, which is/are easy to consume. The bar may be produced by any method known in the art.

The food composition product may be used as a sole source of nutrition of the daily food consumption, or may be used as a replacement for one or more meals throughout the day. As a meal replacement, the food composition product according to the invention supplies the consumer with an inexpensive meal which lowers the expenses for foodstuffs and additional food supplements.

EXAMPLES

Formulation Examples 1 and 2

Natural Balance Shake with Strawberry Flavour

| Ingredient | Example 1 NBS Steviol glycosides (% b.w.) | Example 2 NBS Sucralose (% b.w.) |
| --- | --- | --- |
| Yellow pea protein | 20 | 21 |
| Whole egg | 15 | 15 |
| Apple powder | 12 | 13 |
| Whey powder | 8 | 9 |
| Rosehips Powder | 9 | 9 |
| Whey protein concentrate | 12 | 12 |
| Egg Albumin | 3 | |
| Inulin/oligofructose | 16.4 | 16.4 |

-continued

| Ingredient | Example 1 NBS Steviol glycosides (% b.w.) | Example 2 NBS Sucralose (% b.w.) |
|---|---|---|
| Strawberry Flavor | 1.9 | 1.9 |
| Steviol glycosides | 0.07 | |
| Sucralose | | 0.06 |
| Natural Colorant | 2.2 | 2.2 |
| Ascorbic acid | 0.43 | 0.44 |
| Serving Size | 18.5 | 18.5 |

Figure 2:
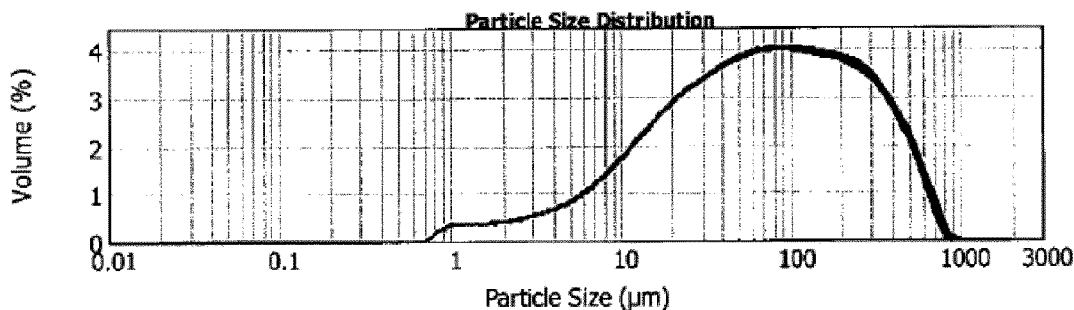

The composition of Example 1 was obtained after milling in a planetary ball mill of the type Fritsch Pulverisette 6. The following FIGS. 1 and 2 show the average particle size distribution prior and after milling. Before milling 10% of the particles showed a size less than 24 µm, 50% less than 200 µm and 90% less than 800 µm. After milling the particle size distribution was as follows: 10% less than 9 µm, 50% less than 70 µm than 90% less than 350 µm.

The product before milling was found to have a gritty and sandy texture and an astringent taste, while the product after milling was found to be smooth, creamy and having more body and a significantly reduced astringent and bitter taste.

The invention claimed is:

1. A dry food composition for mixing with a drinkable liquid, said composition comprising
   (a) carbohydrates,
   (b) proteins,
   (c) fats, and optionally
   (d) probiotic micro-organisms and/or prebiotics, and
   (e) vitamins, minerals, texturisers, fibres, sweeteners, flavourings and/or colorants, whereby said composition shows a particle size distribution wherein
      (i) about 90% by weight of the particles show an average diameter of less than about 400 µm,
      (ii) about 50% by weight of the particles show an average diameter of less than about 80 µm, and
      (iii) about 10% by weight of the particles show an average diameter of less than about 10 µm.

2. The composition of claim 1, wherein said composition when mixed with a drinkable liquid shows glycaemic index (GI) of less than 30.

3. The composition of claim 1, wherein the ratio by weight between carbohydrates, proteins and fat is of the magnitude of about 0.5 to 2.0:1:0.1 to 0.4.

4. The composition of claim 1, wherein the carbohydrates (a) are derived from leguminous plants.

5. The composition of claim 4, wherein the carbohydrates (a) are derived from yellow peas, and rosaceous plants.

6. The composition of claim 1, wherein the carbohydrates (a) are present in the form of simple sugars selected from group consisting of glucose, saccharose, fructose, maltose, lactose and their mixtures.

7. The composition of claim 1, wherein said composition has either a low lactose content or alternatively is completely free of lactose.

8. The composition of claim 1, wherein the proteins (b) are derived from whey, yellow pea, soy, potatoes, lupine, egg albumen, whole eggs or their mixtures.

9. The composition of claim 1, wherein the fats comprise glycerides of omega-3 to omega-6 fatty adds or conjugated linolde add (CLA).

10. The composition of claim 1, wherein the probiotic-microorganisms are selected from lactic acid bacteria and/or bifidobacteriae.

11. The composition of claim 1, wherein the prebiotics are selected from the group consisting of fructoollgosaccha-rides, inulins, isomaltooligosaccha-rides, lactilol, lactosucrose, lactulose, pyrodextrins, soy oligosaccharides, trans-galac-tooligosaccharides, xylooligosaccharides, biopolymers and their mixtures.

12. The composition of claim 1, wherein the vitamins are selected from the group consisting of Vitamin A (retinol, retinal, beta carotene), Vitamin B1 (thiamine), Vitamin B2 (riboflavin), Vitamin B3 (niacin, niacinamide), Vitamin B5 (panthothenic add), Vitamin B6 (pyridoxine, pyridoxamine, paridoxal), Vitamin By (bio-tin), Vitamin B9 (folic add, folinic add), Vitamin B12 (cyanobalamin, hydoxycobalmin, methylcobalmin), Vitamin C (ascorbic add), Vitamin D (cholecaldferol), Vitamin E (tocopherols, tocotrienols), and Vitamin K (phyolloquinone, menaquinone).

13. The composition of claim 1, wherein the minerals are selected from the group consisting of aluminium, antimony, arsenic, barium, beryllium, boron, bromide, cadmium, cerium, caesium, chloride, chrome, dysprosium, iron, erbium, europium, fluoride, gadolinium, gallium, germanium, gold, hafnium, holmium, indium, iridium, iodide, potassium, calcium, cobalt, copper, lanthanum, lithium, lutetium, magnesium, manganese, molybdenum, sodium, neodymium, nickel, niobium, osmium, palladium, phosphorus, platinum, praseodymium, rhenium, rhodium, rubidium, ruthenium, samarium, scandium, sulphur, selenium, silica, silver, strontium, tantalum, tellurium, terbium, thallium, thorium, thulium, titan, vanadium, ytterbium, yttrium, bismuth, wolfram, zinc, tin, zirconium and their mixtures.

14. The composition of claim 1, wherein the sweeteners are selected from the group consisting of sucrose, sucralose, trehalose, lactose, maltose, melicitose, raffinose, palatinose, lactulose, D-ffuctose, D-glucose, D-galactose, L-rhamnose, D-sorbose, D-mannose, D-tagatose, D-arabinose, L-arabinose, D-ribose, D-glyceraldehyde, erythritol, threitol, arabitol, ribitol, xylitol, sorbitol, mannitol, duicitol, lactitol, miraculin, monellin, thaumatin, curculin, brazzein, MAGAP, sodium cyclamate, acesulfame K, neohesperidin dihydrochalcone, saccharine sodium salt, aspartame, super-aspartame, neotame, sucralose, stevioside, rebaudioside, lugduname, carrelame, sucrononate, sucrooctate, glycine, D-leucine, D-threonine, D-asparagine, D-phenylalanine, D-trypto-phan, L-proline, hemandulcin, dihydrochalcone glycosides, glycyrrhetinic acid derivatives, extracts of liquorice {*Glycyrrhizza glabra* ssp.), sugar beet [*Beta vulgaris* ssp.), sugar cane [*Saccharum offldmncm* ssp.), *Lippia* ssp. (e.g. Lip-pia dulds), *Stevia* ssp. (e.g *Stevia rebaudiana*), and Luo Han Guo.

15. The composition of claim 1, wherein the flavourings are selected from the group consisting of natural flavouring substances, extracts or distillates from fruits and vegetables.

16. The composition of claim 1, comprising
   (a) about 10 to about 20% by weight whole eggs;
   (b) about 3 to about 15% by weight egg albumin;
   (c) about 10 to about 25% by weight whey protein concentrate;
   (d) about 10 to about 35% by weight yellow pea protein;
   (e) about 10 to about 25% by weight apple powder; and
   (f) about 5 to about 15% by weight rose hips powder, wherein the optional ingredients are added to make 100% by weight.

17. The composition of claim 1, wherein said composition shows when mixed with a drinkable liquid a pH-value in the range of 5.8 to 6.2.

18. The composition of claim 1, wherein said composition is essentially free of gluten.

19. A non-therapeutic method for improving the over-all health status of a human body by consumption of the food composition of claim 1.

20. A single portion pack, a liquid or a bar containing the food composition of claim 1.

* * * * *